(12) United States Patent
Olivier et al.

(10) Patent No.: US 7,791,734 B2
(45) Date of Patent: Sep. 7, 2010

(54) HIGH-RESOLUTION RETINAL IMAGING USING ADAPTIVE OPTICS AND FOURIER-DOMAIN OPTICAL COHERENCE TOMOGRAPHY

(75) Inventors: Scot S. Olivier, Livermore, CA (US); John S. Werner, Davis, CA (US); Robert J. Zawadzki, Sacramento, CA (US); Sophie P. Laut, Pasedena, CA (US); Steven M. Jones, Livermore, CA (US)

(73) Assignees: Lawrence Livermore National Security, LLC, Livermore, CA (US); University of California, Oakland, CA (US)

( * ) Notice: Subject to any disclaimer, the term of this patent is extended or adjusted under 35 U.S.C. 154(b) by 41 days.

(21) Appl. No.: 11/417,074

(22) Filed: May 2, 2006

(65) Prior Publication Data

US 2007/0258095 A1  Nov. 8, 2007

(51) Int. Cl.
*G01B 9/02* (2006.01)
(52) U.S. Cl. ..................................... 356/479
(58) Field of Classification Search ............... 356/479, 356/497
See application file for complete search history.

(56) References Cited

U.S. PATENT DOCUMENTS

| 2003/0025874 | A1* | 2/2003 | Williams et al. | 351/200 |
|---|---|---|---|---|
| 2005/0157294 | A1* | 7/2005 | Hopkins et al. | 356/328 |
| 2005/0213092 | A1* | 9/2005 | MacKinnon et al. | 356/336 |
| 2006/0058682 | A1* | 3/2006 | Miller et al. | 600/476 |
| 2007/0002327 | A1* | 1/2007 | Zhou et al. | 356/456 |
| 2007/0046948 | A1* | 3/2007 | Podoleanu et al. | 356/497 |

* cited by examiner

*Primary Examiner*—Tarifur Chowdhury
*Assistant Examiner*—Jonathan M Hansen
(74) *Attorney, Agent, or Firm*—John H. Lee

(57) ABSTRACT

This invention permits retinal images to be acquired at high speed and with unprecedented resolution in three dimensions (4×4×6 μm). The instrument achieves high lateral resolution by using adaptive optics to correct optical aberrations of the human eye in real time. High axial resolution and high speed are made possible by the use of Fourier-domain optical coherence tomography. Using this system, we have demonstrated the ability to image microscopic blood vessels and the cone photoreceptor mosaic.

10 Claims, 3 Drawing Sheets

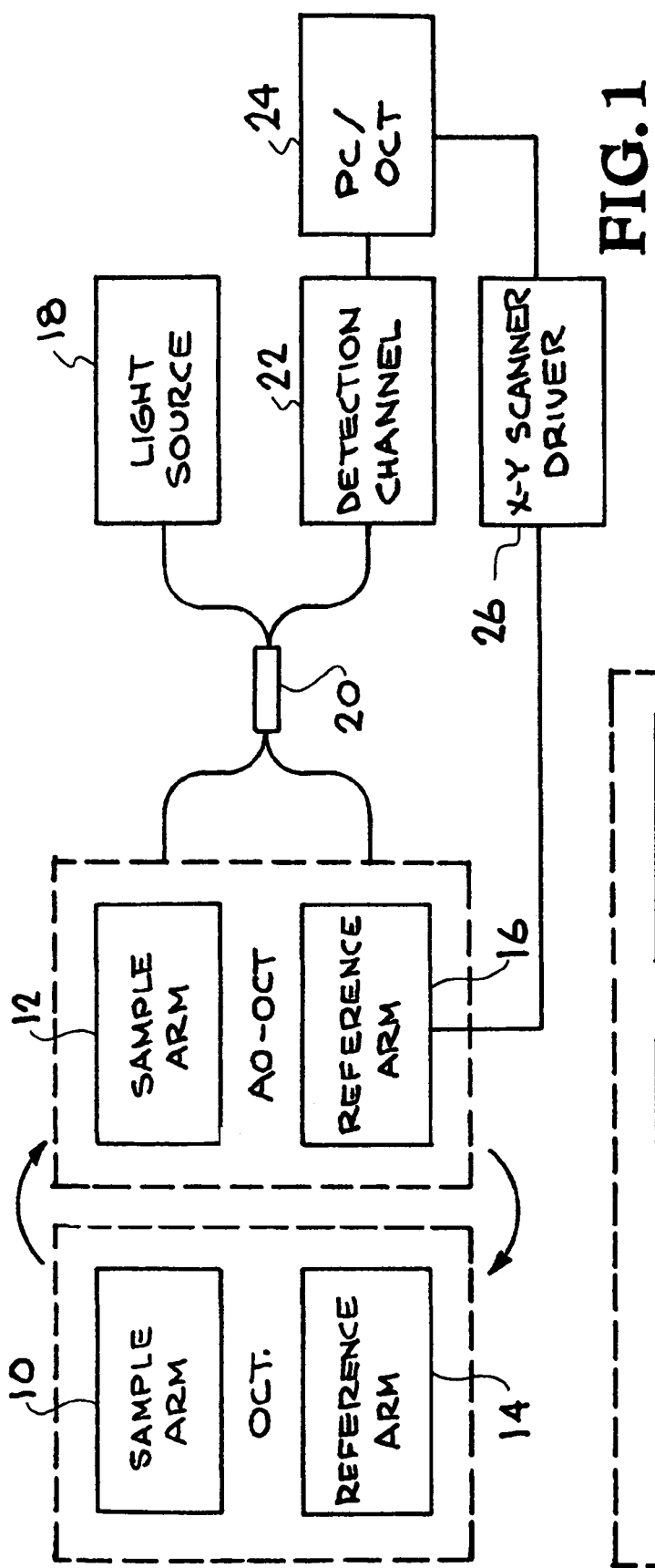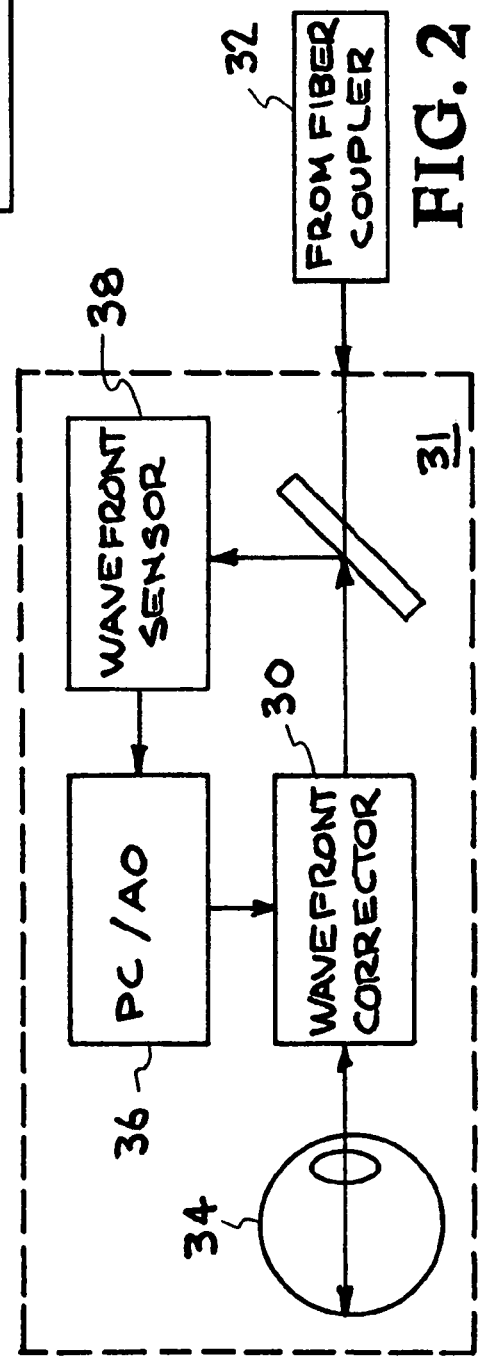

HIGH-RESOLUTION RETINAL IMAGING USING ADAPTIVE OPTICS AND FOURIER-DOMAIN OPTICAL COHERENCE TOMOGRAPHY

The United States Government has rights in this invention pursuant to Contract No. W-7405ENG-48 between the United States Department of Energy and the University of California for the operation of Lawrence Livermore National Laboratory.

BACKGROUND OF THE INVENTION

1. Field of the Invention

The present invention relates to retinal imaging techniques, and more specifically, it relates to technology for the acquisition of retinal images at high speed and with unprecedented resolution in three dimensions.

2. Description of Related Art

Interferometry with broadband light sources has become a widely used technique for imaging in biologic samples using time-domain optical coherence tomography (OCT), optical coherence microscopy (OCM), spectral domain OCT (which encompasses spectrometer based Fourier domain OCT and swept source OCT), color Doppler OCT, and phase-referenced interferometry. In all of these interferometry techniques, light traveling a reference path is mixed with light returning from or traversing a sample on the surface of a single or multiple detectors.

Optical coherence tomography (OCT) is an interferometric, non-invasive optical tomographic imaging technique offering millimeter penetration (approximately 2-3 mm in tissue) with sub-micrometer axial and lateral resolution. The technique was first demonstrated in 1991 with ~30 μm axial resolution. Since then, OCT has achieved sub-micrometer resolution in 2001 due to introduction of wide bandwidth light sources (sources emitting wavelengths over a ~100 nm range). By now OCT has found its place as a widely accepted imaging technique, especially in opthalmology and other biomedical applications With micrometer resolution and cross-sectional imaging capabilities, optical coherence tomography (OCT)[1] has become a prominent biomedical tissue imaging technique; it is particularly suited to ophthalmic applications and in other tissue imaging requiring micrometer resolution and millimeter penetration depth. OCT has critical advantages over other medical imaging systems. Medical ultrasonography, magnetic resonance imaging (MRI) and confocal microscopy are not suited to morphological tissue imaging; the former two having poor resolution; the latter lacking millimeter penetration depth[2,3].

OCT works through the magic of low-coherence interferometry[4,5]. In conventional interferometry with long coherence length (laser interferometry), interference of light occurs over a distance of meters. In OCT, this interference is shortened to a distance of micrometers, thanks to the use of broadband light sources (sources that can emit light over a broad range of frequencies). Light with broad bandwidths can be generated by using superluminescent diodes (superbright LED's) or lasers with extremely short pulses (femtosecond lasers). White light is also a broadband source with lower powers.

Light in an OCT system is broken into two arms—a sample arm (containing the item of interest) and a reference arm (usually a mirror). The combination of backscattered light from the sample arm and reference light from the reference arm gives rise to an interference pattern, but only if light from both arms have traveled the "same" optical distance ("same" meaning a difference of less than a coherence length). By scanning the mirror in the reference arm, a reflectivity profile of the sample can be obtained (this is time domain OCT). Areas of the sample that reflect back a lot of light will create greater interference than areas that don't. Any light that is outside the short coherence length will not interfere. This reflectivity profile, called an A-scan contains information about the spatial dimensions and location of structures within the item of interest. A cross-sectional tomograph (B-scan) may be achieved by laterally combining a series of these axial depth scans (A-scan). Face imaging (C-scan) at an acquired depth is possible depending on the imaging engine used.

In time domain OCT, the pathlength of the reference arm is translated longitudinally in time. A property of low coherence interferometry is that interference, i.e. the series of dark and bright fringes, is only achieved when the path difference lies within the coherence length of the light source. This interference is called auto correlation in a symmetric interferometer (both arms have the same reflectivity), or cross-correlation in the common case. The envelope of this modulation changes as pathlength difference is varied, where the peak of the envelope corresponds to pathlength matching.

The interference of two partially coherent light beams can be expressed in terms of the source intensity, $I_S$, as:

$$I = k_1 I_s + k_2 I_s + 2\sqrt{(k_1 I_s)(k_2 I_s)}(Re[\gamma(\tau)]),$$

where $k_1 + k_2 < 1$ represents the interferometer beam splitting ratio, and $\gamma(\tau)$ is called the complex degree of coherence, i.e., the interference envelope and carrier dependent on reference arm scan or time delay $\tau$, and whose recovery of interest in OCT. Due to the coherence gating effect of OCT the complex degree of coherence is represented as a Gaussian function expressed as[6-].

$$\gamma(\tau) = \exp\left[-\left(\frac{\pi \Delta \nu \tau}{2\sqrt{\ln 2}}\right)^2\right](\exp(-j2\pi\nu_0 \tau))$$

where $\Delta \nu$ represents the spectral width of the source in the optical frequency domain, and $\nu_0$ is the centre optical frequency of the source. In the above equation, the Gaussian envelope is amplitude modulated by an optical carrier. The peak of this envelope represents the location of sample under test microstructure, with an amplitude dependent on the reflectivity of the surface. The optical carrier is due to the Doppler effect resulting from scanning one arm of the interferometer, and the frequency of this modulation is controlled by the speed of scanning. Therefore translating one arm of the interferometer has two functions; depth scanning and a Doppler-shifted optical carrier are accomplished by pathlength variation. In OCT, the Doppler-shifted optical carrier has a frequency expressed as:

$$f_{Dopp} = \frac{2\nu_0 \nu_s}{c}$$

where $\nu_0$ is the central optical frequency of the source, $\nu_s$ is the scanning velocity of the pathlength variation, and c is the speed of light.

The axial and lateral resolutions of OCT are decoupled from one another; the former being an equivalent to the coherence length of the light source and the latter being a function of the optics. The coherence length of a source and hence the axial resolution of OCT is defined as:

$$= \left(\frac{2\ln 2}{\pi}\right)\left(\frac{\lambda_0^2}{\Delta\lambda}\right),$$

$$\approx 0.44\left(\frac{\lambda_0^2}{\Delta\lambda}\right)$$

In frequency domain OCT the broadband interference is acquired with spectrally separated detectors (either by encoding the optical frequency in time with a spectrally scanning source or with a dispersive detector, like a grating and a linear detector array). Due to the Fourier relation (Wiener-Khintchine theorem between the auto correlation and the spectral power density) the depth scan can be immediately calculated by a Fourier-transform from the acquired spectra, without movement of the reference arm[7,8]. This feature improves imaging speed dramatically, while the reduced losses during a single scan improve the signal to noise proportional to the number of detection elements. The parallel detection at multiple wavelength ranges limits the scanning range, while the full spectral bandwidth sets the axial resolution.

Spatially encoded Frequency Domain OCT (also Fourier Domain OCT) SEFD-OCT extracts spectral information by distributing different optical frequencies onto a detector stripe (line-array CCD or CMOS) via a dispersive element. Thereby the information of the full depth scan can be acquired within a single exposure. However, the large signal to noise advantage of FD-OCT is reduced due the lower dynamic range of stripe detectors in respect to single photosensitive diodes, resulting in an SNR (signal to noise ratio) advantage of ~10 dB at much higher speeds. The drawbacks of this technology are found in a strong fall-off of the SNR, which is proportional to the distance from the zero delay and a sinc-type reduction of the depth dependent sensitivity because of limited detection linewidth. (One pixel detects a quasi-rectangular portion of an optical frequency range instead of a single frequency, the Fourier-transform leads to the sinc(z) behavior). Additionally the dispersive elements in the spectroscopic detector usually do not distribute the light equally spaced in frequency on the detector, but mostly have an inverse dependence. Therefore the signal has to be resampled before processing, which can not take care of the difference in local (pixelwise) bandwidth, which results in further reduction of the signal quality.

Time encoded Frequency Domain OCT (also swept source OCT) (TEFD-OCT) tries to combine some of the advantages of standard TD and SEFD-OCT. Here the spectral components are not encoded by spatial separation, but they are encoded in time. The spectrum is either filtered or generated in single successive frequency steps and reconstructed before Fourier-transformation. By accommodation of a frequency scanning light source (i.e., frequency scanning laser) the optical setup becomes simpler than SEFD, but the problem of scanning is essentially translated from the TD-OCT reference-arm into the TEFD-OCT light source. Here the advantage lies in the proven high SNR detection technology, while swept laser sources achieve very small instantaneous bandwidths (=linewidth) at very high frequencies (20-200 kHz). Drawbacks are the nonlinearities in the wavelength, especially at high scanning frequencies. The broadening of the linewidth at high frequencies and a high sensitivity to movements of the scanning geometry or the sample (below the range of nanometers within successive frequency steps).

Focusing the light beam to a point on the surface of the sample under test, and recombining the reflected light with the reference will yield an interferogram with sample information corresponding to a single A-scan (Z axis only). Scanning of the sample can be accomplished by either scanning the light on the sample, or by moving the sample under test A linear scan will yield a two-dimensional data set corresponding to a cross-sectional image (X-Z axes scan), whereas an area scan achieves a three-dimensional data set corresponding to a volumetric image (X-Y-Z axes scan), also called full-field OCT.

Systems based on single point, or flying-spot time domain OCT, must scan the sample in two lateral dimensions and reconstruct a three-dimensional image using depth information obtained by coherence-gating through an axially scanning reference arm. Two dimensional lateral scanning has been electromechanically implemented by moving the sample[8] using a translation stage, and using a novel micro-electro-mechanical system scanner[10].

Parallel OCT using a charge-coupled device (CCD) camera has been used in which the sample is full-field illuminated and en face imaged with the CCD, hence eliminating the electromechanical lateral scan. By stepping the reference mirror and recording successive en face images a three-dimensional representation can be reconstructed. Three-dimensional OCT using a CCD camera was demonstrated in a phase-stepped technique[11], using geometric phase-shifting with a Linnik interferometer[12], utilising a pair of CCDs and heterodyne detection[13], and in a Linnik interferometer with an oscillating reference mirror and axial translation stage[14]. Central to the CCD approach is the necessity for either very fast CCDs or carrier generation separate to the stepping reference mirror to track the high frequency OCT carrier.

A two-dimensional smart detector array, fabricated using a 2 μm complementary metal-oxide-semiconductor (CMOS) process, was used to demonstrate full-field OCT[15]. Featuring an uncomplicated optical setup, each pixel of the 58×58 pixel smart detector array acted as an individual photodiode and included its own hardware demodulation circuitry.

REFERENCES

1. D. Huang, E. A. Swanson, C. P. Lin, J. S. Schuman, W. G. Stinson, W. Chang, M. R. Hee, T. Flotte, K Gregory, C. A. Puliafito and J. G. Fujimoto, "Optical Coherence Tomography", *Science*, vol. 254, no. 5035, pp. 1178-1181, 1991.
2. W. Drexler, U. Morgner, R. K. Ghanta, J. S Schuman, F. X Kärtner, J. G. Fujimoto, *Nature Medicine,* 2001.
3. S. C. Kaufman, D. C. Musch, M. W. Belin, E. J. Cohen, D. M. Meisler, W. J. Reinhart, I. J. Udell and W. S. V. Meter, "Confocal Microscopy: A Report by the American Academy of Opthalmology", *Opthalmology, vol.* 111, no. 2, pp. 396-496, 2004.
4. S. J. Riederer, "Current technical development of magnetic resonance imaging," *IEEE Engineering in Medicine and Biology Magazine*, vol. 19, no. 5, pp. 34-41, 2000. Available: ieee.org.
5. M. Born and E. Wolf, *Principles of Optics: Electromagnetic Theory of Propagation, Interference and Diffraction of Light*, Cambridge, Cambridge University Press, 1999.
6. A. F. Fercher, K. Mengedoht, W. Werner, "Eye length measurement by interferometry with partially coherent light," *Optics Letters* vol. 13, no. 3, pp. 186-188, 1988. Available: opticsinfobase.org.
7. J. M. Schmitt, "Optical Coherence Tomography (OCT): A Review", *IEEE Selected Topics in Quantum Electronics*, vol. 5, no. 4, pp. 1205-1215, 1999. Available: ieee.org.

8. A. F. Fercher, C. K Hitzenberger, C. K Kamp and S. Y. El-Zayat, "Measurement of intraocular distances by backscattering spectral interferometry," *Optics Communications* vol. 117, no. 1-2, pp. 43-48, (1995. Available: http://dx.doi.org/10.1016/0030-4018(95)00119-S sciencedirect.com].
9. J. M. Herrmann, M. E. Brezinski, B. E. Bouma, S. A. Boppart, C. Pitris, J. F. Southern and J. G. Fujimoto, "Two- and three-dimensional high-resolution imaging of the human oviduct with optical coherence tomography," *Fertility and Sterility*, vol. 70, no. 1, pp. 155-158, 1998. Available: sciencedirect.com.
10. J. T. W. Yeow, V. X. D. Yang, A. Chahwan, M. L. Gordon, B. Qi, I. A. Vitkin, B. C. Wilson and A. A. Goldenberg, "Micromachined 2-D scanner for 3-D optical coherence tomography," *Sensors and Actuators A*, vol. 117, no. 2, pp. 331-340, 2004. Available: sciencedirect.com.
11. C. Dunsby, Y. Gu and P. M. W. French, "Single-shot phase-stepped wide-field coherence gated imaging," Optics Express, vol. 11, no. 2, pp. 105-115, 2003. Available: opticsinfobase.org.
12. M. Roy, P. Svahn, L. Cherel and C. J. R. Sheppard, "Geometric phase-shifting for low-coherence interference microscopy," *Optics and Lasers in Engineering*, vol. 37, no. 6, pp. 631-641, 2002. Available: sciencedirect.com.
13. M. Akiba, K P. Chan and N. Tanno, "Full-field optical coherence tomography by two-dimensional heterodyne detection with a pair of CCD cameras," *Optics Letters*, vol. 28, no. 10, pp. 816-818, 2003. Available: opticsinfobase.org.
14. A. Dubois, L. Vabre, A.-C. Boccara and E. Beaurepaire, "High-resolution full-field optical coherence tomography with a Linnik microscope," *Applied Optics*, vol. 41, no. 4, pp. 805-812, 2002. Available: opticsinfobase.org.
15. S. Bourquin, P. Seitz and R P. Salathé, "Optical coherence tomography based on a two-dimensional smart detector array," *Optics Letters*, vol. 26, no. 8, pp. 512-514, 2001. Available: opticsinfobase.org.

SUMMARY OF THE INVENTION

It is an object of the present invention to enable the acquisition of retinal images at high speed and with unprecedented resolution in three dimensions.

Another object is to provide high lateral resolution of retinal images by using adaptive optics to correct optical aberrations of the human eye in real time.

Still another object is to provide high speed acquisition of high axial resolution retinal images by the use of Fourier-domain optical coherence tomography.

Another object is to image microscopic blood vessels and the cone photoreceptor mosaic.

An additional object is to image axon bundles within the nerve fiber layer.

These and other objects will be apparent based on the disclosure herein.

The instrument uses adaptive optics (AO) and optical coherence tomography (OCT). An exemplary AO-OCT system according to the present invention has been reduced to practice within a 1 m$^2$ area on a standard laboratory optical table. The sample arm utilizes a Hartmann-Shack wavefront sensor and a 35-electrode bimorph deformable mirror for aberration correction in its present configuration. The lateral resolution is further improved by introducing a second deformable mirror using a commercial microelectromechanical system (MEMs). A key advantage of the present system is that the same light source is used for both OCT and Hartmann-Shack detection channels, allowing simultaneous operation of AO and OCT. Two independent PCs are used, one for AO control (AO-PC) and one for the OCT scanning and detection unit (OCT-PC). Separate sample and reference arms are constructed on the same table to test the OCT system with and without AO. A bite-bar, forehead-rest assembly is mounted on an X-Y-Z translation stage to permit precise positioning of the subject's eye. This may also be accomplished with a chin and forehead rest mounted to a height-adjustable table and slit-lamp-like device. An image from the wavefront sensor is used to monitor the X-Y position of the eye's pupil while fixation is directed to an external target to minimize head and eye motion and to allow precise imaging of different retinal locations. Although not necessary, to ensure the maximum pupil size and minimize fluctuations in accommodation, the subject's eye is dilated and cyclopleged with 2.5% Phenylephrine and 1% Tropicamide.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 1 is a schematic of an OCT engine.

FIG. 2 is a schematic of an AO-control system.

DETAILED DESCRIPTION OF THE INVENTION

Figure 3B:
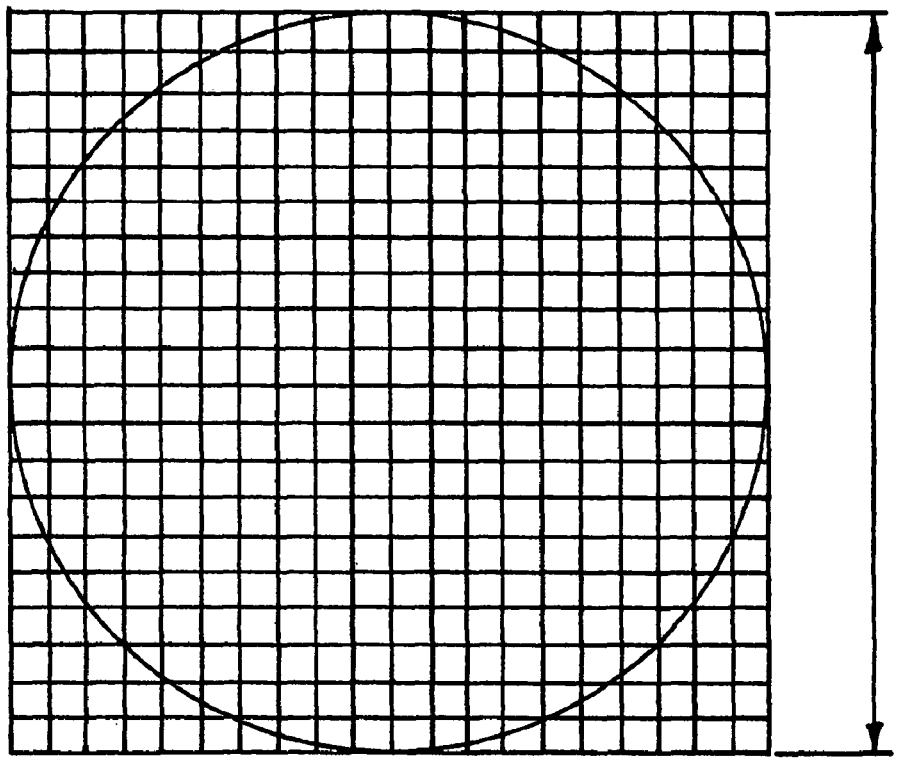
FIG. 3B shows a Hartmann-Shack 400-lenslet configuration.

The Fourier-domain OCT system uses the spectral OCT approach in which a high-efficiency spectrometer measures the spectrum of the light that returns from reference and sample arms. FIG. 1 shows a schematic of the OCT engine according to a test where two sample arms, 10 and 12 and two reference arms 14 and 16 were constructed for AO-OCT and OCT imaging. A standard fiber-based OCT instrument is operated in Michelson interferometer configuration, where FC/APC fiber connectors are used to connect the fiber coupler's (80/20 splitting ratio) two outputs to fiber collimators placed at the input of bulk optics of the sample and reference arms. This feature of the OCT engine (light source 18, fiber coupler 20, detection channel 22) allows interchangeable operation for both AO-OCT and standard OCT imaging. Computer 24 controls X-Y Scanner driver 26 and collects and analyzes data from detection channel 22. Simple reconnection of FC/APC fiber connectors allowed rapid switching between the two systems. The purpose of this configuration to test the concept and show that the AO-OCT system performed better as well as allowing for other circumstances where OCT without AO is desired. The AO may be substituted with a wavefront corrector such as a liquid crystal spatial light modulator.

In order to gain access to depth information carried by back-scattered light from the sample arm, it must be combined with light back-reflected from the reference arm, consisting of a mirror placed at the proper optical path length, and sent to the detection channel where the spectral interference pattern is recorded. This spectral information, as seen by the spectrometer's CCD camera, can be described as:

$$I(k) = I_r(k) + I_s(k) + 2\sqrt{I_r(k)I_s(k)} \sum_n \alpha_n \cos(kz_n) \quad (1)$$

where $I_r(k)$, $I_s(k)$ refer to wavelength-dependent intensities from reference and sample arms, respectively; k is wave number; and, $\alpha_n$ is the square root of sample reflectivity at depth $z_n$. The depth information (the equivalent of an A-scan in the time-domain) is accessed by $FTT^{-1}$ of the spectrometer signal:

$$I(z) = |FT^{-1}[I(k)]|^2 \quad (2)$$
$$= \Gamma^2(z) \otimes \left\{ \delta(0) + \sum_n \alpha_n^2 \delta(z \pm z_n) + O[I_s^2/I_r^2] \right\}$$

where $\Gamma(z)$ is the envelope of the coherence function. To remove the autocorrelation term $\delta(0)$ and "coherence artifacts," $O[I_s^2/I_r^2]$ in Eq. 2, the DC subtraction already described by other groups can be used. To overcome the problem of the complex conjugate image present after implementation of the Inverse Fourier Transform, only one half the image is displayed and the whole retina is placed on a negative path length difference side with respect to the reference mirror position.

As already noted, the light from the sample and reference arms is split in the fiber coupler and sent via fiber to the detection channel consisting of a science grade custom-built spectrometer. At the input of this channel the light is collimated using a 100 mm focal length collimating objective (see, e.g., OZ optics) and sent to the 1200 l/mm holographic transmitting diffraction grating (Wasatch Photonics). A custom-design objective (triplet) having 150 mm focal length is used to focus the light onto the CCD. The detection spectrometer uses a CCD line-scan camera (12 bit, Atmel, 2048-pixels) which samples the spectrum with 0.066 nm spectral spacing, $\delta\lambda$. The OCT computer is a dual processor Intel Xeon 3.6 GHz with 3 GB RAM memory. The standard system settings allow acquisition rates varying from 9 Frames/s (1000 A-scans/Frame; 100 µs exposure) to 36 Frames/s (500 A-scans/Frame; 50 µs exposure). Custom C++ based software developed at Duke University fully processes (including re-sampling from $\lambda$ to k, dispersion compensation to third order, and FFT), displays, and streams B-scan data to system memory in real time at the same frame rates, allowing the operator to track and eliminate streamed data affected by eye motion or eye blinking. Two main scanning settings for 3D image acquisition were used: 100 B-scans/volume (with 1000 A-scans/B-scan) and 200 B-scans/volume (with 500 A-scans/B-scan). In both cases, the full volume acquisition time was less then 6 s for 50 µs A-scan exposures. After finishing acquisition, depending on the scanning pattern settings, the raw data of the last 100 or 200 frames are optionally streamed to the PC's hard drive. These data may be later post-processed in LabVIEW using numerical dispersion compensation methods previously described by Wojtkowski et al. and zero-padding techniques to further enhance image quality. With the current spectrometer design, the maximum axial range (seen after Fourier Transform) is 2.7 mm in free space, corresponding to approximately 2 mm in the eye.

The heart of the OCT engine is a fiber-based Michelson interferometer. Two light sources, superluminescent diodes (SLD) from Superlum ($\lambda_0$=841 nm, $\Delta\lambda$=50 nm, P=8 mW) and ($\lambda_0$=890 nm, $\Delta\lambda$=140 nm, P=7.3 mW) have been used, with estimated axial resolution of $\Delta z$=6 µm and 3.5 µm, respectively, in the retina. The spectrum of the first SLD was imaged on 1024 pixels of the CCD while the second one used all 2048 pixels. The power at the subject's eye is 400 µW for the AO-OCT system and 700 µW for the OCT system, below the ANSI maximum recommended exposure levels.

The reference DC file can be updated before each test to remove the coherent noise in the images. An OCT/PC drives the two x- and y-galvo scanners allowing different scanning modes: standard B-scans, radial, circular as well as 3D acquisition for both AO-OCT and OCT instruments.

FIG. 2 shows a schematic of an AO system control. The adaptive optics (AO) system 30 is positioned in the sample channel 31 of the AO-OCT instrument between the fiber 32 and subject's eye 34. The main advantage of this approach is that the imaging beam is corrected before entering the eye and on the exit path from the eye to the detector. This ensures equal spot size and imaging resolution with the most efficient light usage. One of the drawbacks of this approach is the requirement of a long reference arm to match the sample arm length; in the one case, it is equal to about 7 m. The AO-control software used in the system was developed at Lawrence Livermore National Laboratory.

The AO-control computer (PC/AO) 36 reads the data from the Hartmann-Shack wavefront sensor 38 (the combination of a lenslet array and a CCD camera are placed in the focal plane of sensor 38) and uses it as a reference for wavefront correction. The sensor is a Dalsa 1M60 CCD CameraLink camera with a 20×20 lenslet array (Adaptive Optics Associates, 0500-3-S-A) having 500-µm pitch and 30 mm focal length.

Figure 3A:
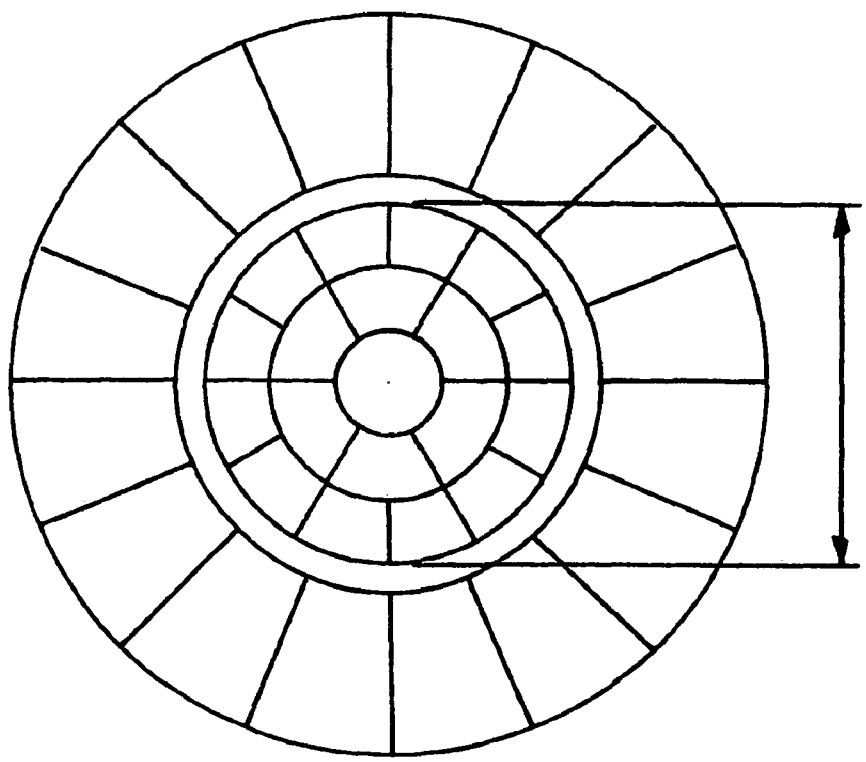
FIG. 3A shows a actuator geometry for a 35-element AOptix DM.

FIG. 3A shows the actuator geometry for the 35-element AOptix DM and FIG. 3B shows the Hartmann-Shack 400-lenslet configuration. The center 10 mm area of FIG. 3A corresponds to an image of a 7 mm eye pupil diameter. Note different scales for DM and lenslet array. The circular array of the 284 lenslets is at a conjugate plane with the eye pupil and sees the 8% of the OCT light back-reflected from the retina that is redirected by a 8/92 pellicle beam-splitter. The eye pupil plane is magnified 1.44 times so that the wavefront at the pupil plane is sampled with center-to-center spacing of 348 µm. The wavefront sensor measures centroids, i.e., displacements of the spots produced by the lenslet array from its reference position. These values are then multiplied by a control matrix that determines the array of voltages to drive the actuators of the deformable mirror. The control matrix is calculated as an inverse of the system matrix measured experimentally. Since closed-loop adaptive optics are used in this instrument, the centroid values from the wavefront sensor are measured at the beginning of each loop and are then used to find new (updated) voltage values to shape the deformable mirror. This system operates at 25 Hz; the global control loop performs the correction of aberrations with the same temporal frequency.

In once embodiment, a 35-element, bimorph DM from AOptix Technologies, Inc is used as the wavefront corrector. It consists of two layers of ceramic lead magnesium niobate (PMN) that are directly actuated by the electrodes bonded on the material. PMN material deforms when an electric field is applied, allowing total stroke of ~32 µm. The magnification factor, $\gamma$, between the eye pupil plane and DM planes was based upon the physical dimensions of the wavefront corrector and equals 1.43 for the AOptix DM (10 mm diameter pupil image). Note that even though only 19 inner actuators (curvature deformation actuators) of the bimorph mirror are covered by the image of the pupil, all 35 elements of the DM including 16 outer ring actuators (slope actuators) are used to correct the wavefront.

The AOptix bimorph DM is capable of correcting relatively large defocus and spherical aberrations owing to its maximum stroke of ±16 µm. However, as the order of Zernike modes increases, there is an increase in the residual wavefront error. For this reason, incorporation of a second DM will improve the optical correction. Even using the single bimorph DM, it is possible to introduce arbitrary amounts of defocus to shift the focal plane of the imaging instrument while still correcting the remaining aberrations. This is an important feature of the instrument because only the depth range on the order of 50-60 µm (for diffraction-limited performance with pupil diameter of 6-7 mm) is located in the near field of the focusing spot and offers the best lateral resolution. Thus, to exploit the superior lateral resolution of our AO-OCT system, the focal plane of the instrument should be shifted towards the structure of interest. As a rule of thumb, one-quarter diopter of defocus shifts the focal plane on the retina by ~93 µm. Another important advantage of using the DM for shifting focus is that the path length in the sample arm stays constant. This is critical for imaging with FD-OCT where any change in the sample arm length would shift the image and force the operator to compensate for it by moving the mirror in the reference arm. In our case, no active compensation is necessary. The current AO-control software allows seven pre-defined settings of the DM to create arbitrary defocus in the pupil plane, which was sufficient to shift the focus through all retinal layers of interest. The result of shifting focus is an increase in intensity due to better coupling of reflected light from the imaged structures.

The control of the deformable mirror for AO requires the use of the classical singular value decomposition (SVD) method, already well described in the literature, to generate the set of voltages associated with the reconstruction of a specific wavefront.

The optical design of the sample arm consists of a series of afocal telescopes that conjugate the eye pupil plane with all key components of the system: x and y scanning mirrors (which limits scanner motion error observed on the wavefront sensor), the bimorph deformable mirror and the Hartmann-Shack wavefront sensor. The AO-OCT system was designed with spherical mirrors, instead of lenses commonly used in OCT sample arms, to reduce dispersion matching problems as well as back reflections that can occur while the scanners are moving (which may reduce performance of the H-S wavefront sensor). One of the problems with such a design is that spherical mirrors are used in off-axis configuration which introduces static aberration. This problem is reduced by using mirrors with long focal lengths.

Figure 4:
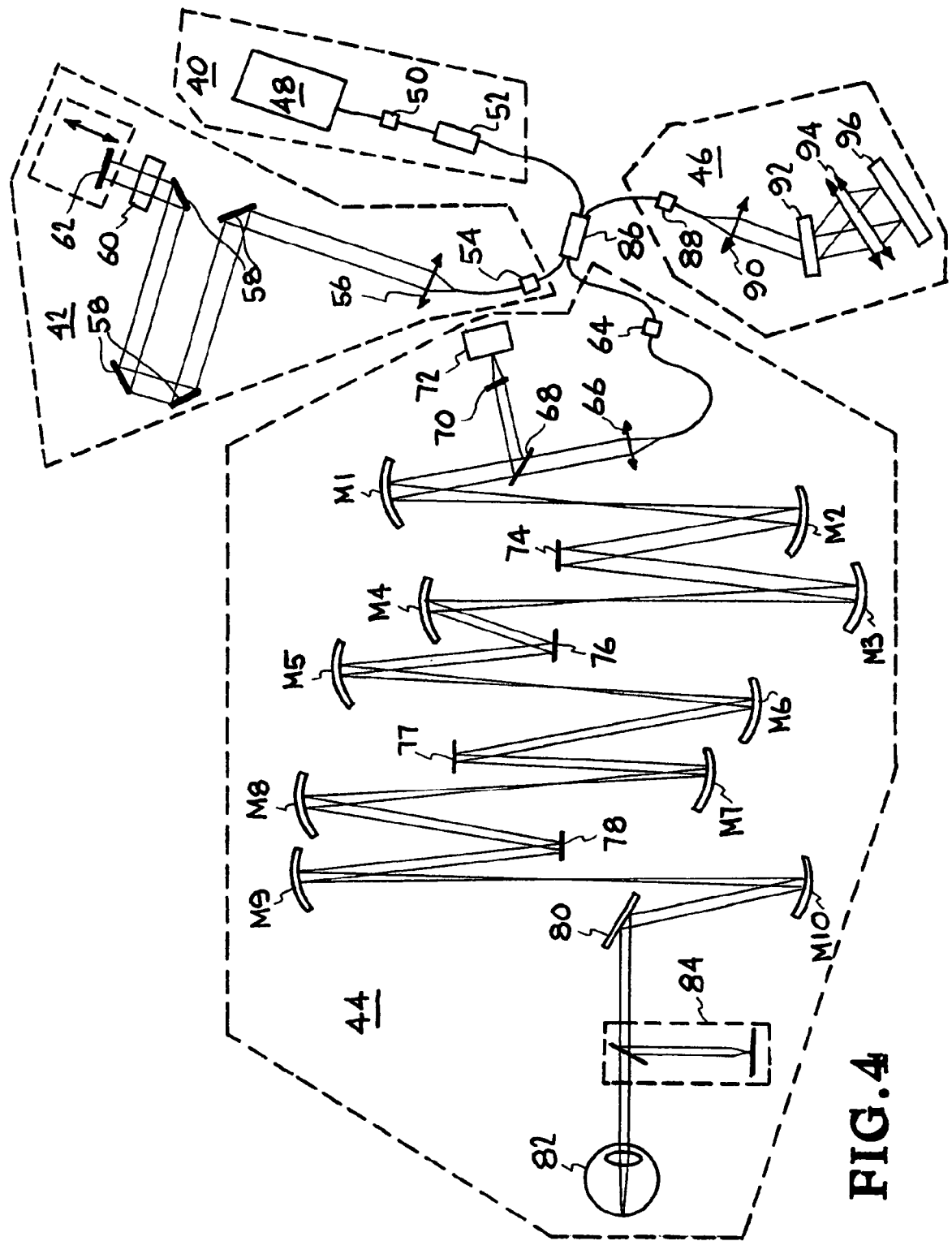
FIG. 4 is a schematic of an AO-OCT experimental setup constructed on a standard laboratory optical table occupying 1×1 m.

FIG. 4 is a schematic of an AO-OCT experimental setup constructed on a standard laboratory optical table occupying 1×1 m. The reference arm length has been shortened on the illustration for simplification. Key: γ—magnification, D—diameter, DM—deformable mirror; M1-M10—spherical mirrors, P—pupil plane, R—retinal plane. The figure shows a fiber-based system comprising a light delivery arm 40, a reference arm 42, a sample arm 44 and a detection arm 46. The light delivery arm includes a super luminescent diode 48, polarization control 50 and Faraday isolator 52. The reference arm includes polarization control 54, a fiber collimator 56, path folding mirrors 58, a water cuvet 60 and a translatable mirror 62. The sample arm includes polarization control 64, a fiber collimator 66, a beamsplitter 68 configured to reflect light to lenslet array 70 and CCD camera 72 on the return path, a series of curved mirrors M1-M9, deformable mirror 74, two mirror 76, X-scanner mirror 77 and Y-scanner mirror 78, pointing mirror 80 for directing the beam to a subject's eye 82 and a removable mirror/model eye combination 84. An 80/20 fiber coupler 86 directs the light to the reference and sample arm and sends the light to the detection channel 46, which includes polarization control 88, fiber collimator 90, diffraction grating 92, focusing optics 94 and CCD line 96.

The scanning field of view of the instrument illustrated in FIG. 4 allows imaging of up to ±1.5 deg or 1 mm patches of retina, as compared to ±12 deg or 8 mm scanning range commonly used in commercial instruments (Stratus OST, Carl Zeiss Meditec). This value has been chosen due to the limited isoplanatic angle for the human eye. As already mentioned, lack of back reflections allows simultaneous wavefront measurement and correction during OCT system operation to compensate for some dynamic ocular aberrations that would otherwise compromise OCT image quality. To match the dispersion of the sample arm, a water vial (25 mm length) is placed in the reference arm. This instrument has higher lateral and axial resolution than commercial instruments used for retinal imaging. The higher lateral resolution is due to the use of adaptive optics, not found in commercial OCT instruments. The higher axial resolution is due to use of higher bandwidth sources than in commercial instruments and also the use of Fourier-domain OCT—commercial instruments operate in the time domain. Fourier-domain OCT in the present instrument is about 50 times faster than time-domain commercial instruments.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. An apparatus, comprising:

a Michelson interferometer comprising a fiber-optic based optical coherence tomography (OCT) configuration and including an input arm, a reference arm, a sample arm and a detection arm, wherein said fiber optic based OCT configuration comprises a fiber optic splitter including an input arm fiber optic, a reference arm fiber optic, a sample arm fiber optic and a detection arm fiber optic, wherein said input arm comprises only one light source configured for coupling light into said input arm fiber optic to produce input light, wherein said input light travels from said input arm fiber optic through said splitter and out of said sample arm fiber optic and said reference arm fiber optic into said sample arm and said reference arm respectively to produce sample arm light and reference arm light respectively, wherein only said sample arm comprises a first wavefront corrector, a second wavefront corrector and a wavefront sensor, wherein said first wavefront corrector and said second wavefront corrector are configured to correct for wavefront error of the human eye, wherein said first wavefront corrector comprises a first deformable mirror, wherein said second wavefront corrector comprises a second deformable mirror operatively connected to a microelectromechanical system, wherein said reference arm does not comprise an adaptive optic, wherein said sample arm light travels to a target located at the end of said sample arm to produce target light, wherein at least a portion of said target light travels in a reverse direction along said sample arm, into said sample arm fiber optic and passes through said splitter to produce return target light, wherein said return sample arm light travels from said splitter and into said detection arm fiber optic to produce detection arm sample light, wherein said reference arm light travels to the end of said reference arm and is reflected by a reference arm mirror to produce reflected reference arm light, wherein said reflected reference arm light travels in a reverse direction along said reference arm, into said reference arm fiber optic and through said splitter to produce return reference arm light, wherein said return reference arm light travels from said splitter and into said detection arm fiber optic to produce detection arm reference light, wherein said detection arm sample light and said detection arm reference light combine to produce interference light, wherein said detection arm comprises a spectrometer, wherein said interference light is directed to said spectrometer to produce spectrometer data; and means for analyzing said spectrometer data to produce Fourier-domain OCT data.

2. The apparatus of claim 1, wherein said spectrometer comprises a transmitting diffraction grating.

3. The apparatus of claim 2, wherein said transmitting diffraction grating comprises a holographic transmitting diffraction grating.

4. The apparatus of claim 2, wherein said spectrometer further comprises a CCD line-scan camera.

5. A method, comprising:
directing light into a Michelson interferometer comprising a fiber-optic based optical coherence tomography (OCT) configuration and including an input arm, a reference arm, a sample arm and a detection arm, wherein said fiber optic based OCT configuration comprises a fiber optic splitter including an input arm fiber optic, a reference arm fiber optic, a sample arm fiber optic and a detection arm fiber optic, wherein said input arm comprises only one light source configured for coupling light into said input arm fiber optic to produce input light, wherein said input light travels from said input arm fiber optic through said splitter and out of said sample arm fiber optic and said reference arm fiber optic into said sample arm and said reference arm respectively to produce sample arm light and reference arm light respectively, wherein only said sample arm comprises a first wavefront corrector, a second wavefront corrector and a wavefront sensor, wherein said first wavefront corrector and said second wavefront corrector are configured to correct for wavefront error of the human eye, wherein said first wavefront corrector comprises a first deformable mirror, wherein said second wavefront corrector comprises a second deformable mirror operatively connected to a microelectromechanical system, wherein said reference arm does not comprise an adaptive optic, wherein said sample arm light travels to a target located at the end of said sample arm to produce target light, wherein at least a portion of said target light travels in a reverse direction along said sample arm, into said sample arm fiber optic and passes through said splitter to produce return target light, wherein said return sample arm light travels from said splitter and into said detection arm fiber optic to produce detection arm sample light, wherein said reference arm light travels to the end of said reference arm and is reflected by a reference arm mirror to produce reflected reference arm light, wherein said reflected reference arm light travels in a reverse direction along said reference arm, into said reference arm fiber optic and through said splitter to produce return reference arm light, wherein said return reference arm light travels from said splitter and into said detection arm fiber optic to produce detection arm reference light, wherein said detection arm sample light and said detection arm reference light combine to produce interference light, wherein said detection arm comprises a spectrometer, wherein said interference light is directed to said spectrometer to produce spectrometer data;

positioning an object to be imaged in said sample arm; and analyzing said spectrometer data to produce Fourier-domain OCT data.

6. The method of claim 5, wherein said spectrometer comprises a diffraction grating.

7. The method of claim 6, wherein said diffraction grating comprises holographic transmitting diffraction grating.

8. The method of claim 6, wherein said spectrometer further comprises a CCD line-scan camera.

9. An apparatus, comprising:
a single source of input light;
a fiber optic splitter comprising a source light collection fiber optic, a reference fiber optic, a signal fiber optic and a detection fiber optic, wherein said source light collection fiber optic is positioned to collect said input light, wherein said splitter will transmit a first portion of said input light into said reference fiber optic to produce reference light and will further transmit a second portion of said input light into said signal fiber optic to produce signal light;

a signal arm comprising:
means for collecting said signal light as it exits said signal fiber optic to produce first collected signal light;
a deformable mirror (DM) operatively positioned to receive and reflect said first collected signal light to produce reflected DM light;
first means for scanning said reflected DM light to produce first scanned light;
second means for scanning said first scanned light to produce second scanned light;
means for directing said second scanned light onto a target to produce target light, wherein a portion of said target light will propagate to said second means and then to said first means and then to said DM to produce return light, wherein said return light will then propagate to means for splitting said return light which will produce transmitted return signal light and a reflected return signal light, wherein said transmitted return signal light will be collected by said means for collecting and then will be directed into said signal fiber optic to produce collected return signal light;
means for analyzing said reflected return signal light to produce wavefront data; and means for analyzing said wavefront data and altering the surface of said DM;

a reference arm comprising:
  means for collecting said reference light as it exits said reference fiber optic to produce reference light;
  a reference mirror (RM); and
  means for directing said reference light onto said RM, wherein said RM will reflect said reference light to produce reflected reference light, wherein said reflected reference light will propagate back to said means for collecting said reference light which will collect and direct said reflected reference light into said reference fiber optic to produce collected return reference light, wherein said collected return signal light and said collected return reference light will be transmitted by said splitter into said detection fiber optic; and a detection arm comprising:
  means for collecting said collected return signal light and said collected return reference light as they exit said detection fiber optic to produce interference light;
  a spectrometer positioned to collected said interference light to produce spectrometer data; and
  means for analyzing said spectrometer data to produce Fourier-domain OCT data.

10. A method, comprising:
providing an interferometer comprising:
a single source of input light;
a fiber optic splitter comprising a source light collection fiber optic, a reference fiber optic, a signal fiber optic and a detection fiber optic, wherein said source light collection fiber optic is positioned to collect said input light, wherein said splitter will transmit a first portion of said input light into said reference fiber optic to produce reference light and will further transmit a second portion of said input light into said signal fiber optic to produce signal light;

a signal arm comprising:
  means for collecting said signal light as it exits said signal fiber optic to produce first collected signal light;
  a deformable mirror (DM) operatively positioned to receive and reflect said first collected signal light to produce reflected DM light;
  first means for scanning said reflected DM light to produce first scanned light;
  second means for scanning said first scanned light to produce second scanned light;
  means for directing said second scanned light onto a target to produce target light, wherein a portion of said target light will propagate to said second means and then to said first means and then to said DM to produce return light, wherein said return light will then propagate to means for splitting said return light which will produce transmitted return signal light and a reflected return signal light, wherein said transmitted return signal light will be collected by said means for collecting and then will be directed into said signal fiber optic to produce collected return signal light;
  means for analyzing said reflected return signal light to produce wavefront data; and
  means for analyzing said wavefront data and altering the surface of said DM;

a reference arm comprising:
  means for collecting said reference light as it exits said reference fiber optic to produce reference light;
  a reference mirror (RM); and
  means for directing said reference light onto said RM, wherein said RM will reflect said reference light to produce reflected reference light, wherein said reflected reference light will propagate back to said means for collecting said reference light which will collect and direct said reflected reference light into said reference fiber optic to produce collected return reference light, wherein said collected return signal light and said collected return reference light will be transmitted by said splitter into said detection fiber optic; and a detection arm comprising:
  means for collecting said collected return signal light and said collected return reference light as they exit said detection fiber optic to produce interference light;
  a spectrometer positioned to collected said interference light to produce spectrometer data; and
  means for analyzing said spectrometer data to produce Fourier-domain OCT data;

directing said input light into said source light collection fiber optic, wherein said spectrometer data is produced; and analyzing said spectrometer data to produce Fourier-domain OCT data.

* * * * *